United States Patent [19]

Tosi et al.

[11] 4,189,499
[45] Feb. 19, 1980

[54] LYSINE 4-ALLYLOXY-3-CHLOROPHENYLACETATE AND METHOD OF ITS PREPARATION

[75] Inventors: Carlo Tosi, Milan; Pierarturo Ferlenghi, Plan Di Arese, both of Italy

[73] Assignee: Biochefarm S.A., Switzerland

[21] Appl. No.: 13,083

[22] Filed: Feb. 21, 1979

Related U.S. Application Data

[63] Continuation of Ser. No. 777,896, Mar. 16, 1977, abandoned.

[51] Int. Cl.$^2$ .................. C07C 101/04; A61K 31/205
[52] U.S. Cl. ................................ 424/316; 260/501.11
[58] Field of Search .................... 260/501.11; 424/316

[56] References Cited

U.S. PATENT DOCUMENTS

| 3,658,889 | 4/1972 | Suverkropp | 260/501.11 |
| 3,824,277 | 7/1974 | Buu-Hoi et al. | 562/465 |

FOREIGN PATENT DOCUMENTS

| 2419317 | 9/1975 | Fed. Rep. of Germany | 260/501.11 |
| 2508895 | 9/1975 | Fed. Rep. of Germany | 260/501.11 |
| 385222 | 11/1970 | Spain | 260/501.11 |

OTHER PUBLICATIONS

Martin, Remington's Pharm. Sciences, Mack Publishing Co., pp. 180–181 (1965).

Primary Examiner—James O. Thomas, Jr.
Assistant Examiner—G. T. Breitenstein
Attorney, Agent, or Firm—Gordon W. Hueschen

[57] ABSTRACT

Lysine 4-allyloxy-3-chlorophenylacetate is a salt of Alclofenac which is soluble in biological fluids and particularly adapted for intravenous or intramuscular administration. Its method of preparation consists in reacting Alclofenac with lysine carbonate in hydroalcoholic solution and separating the corresponding salt by adding precipitants or by concentrating the hydroalcoholic solution.

4 Claims, 4 Drawing Figures

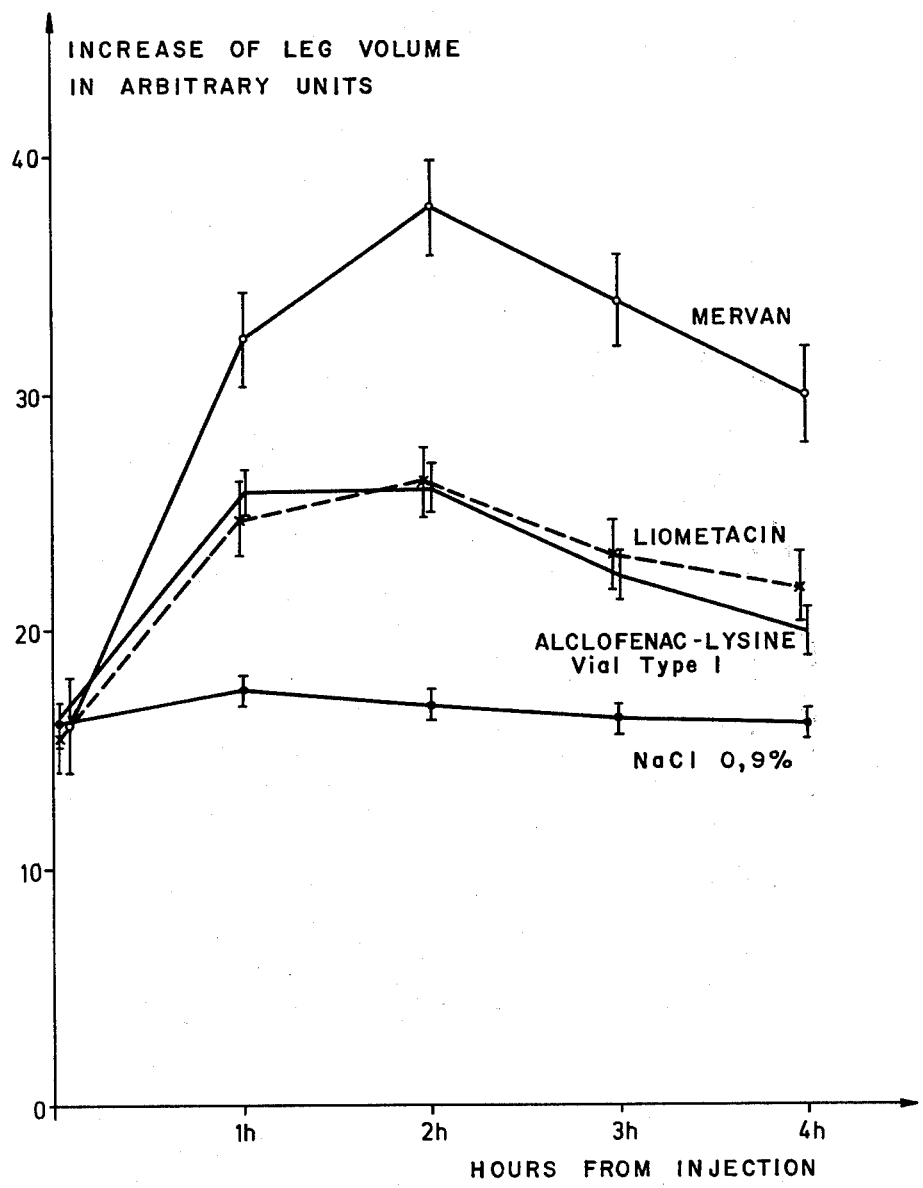

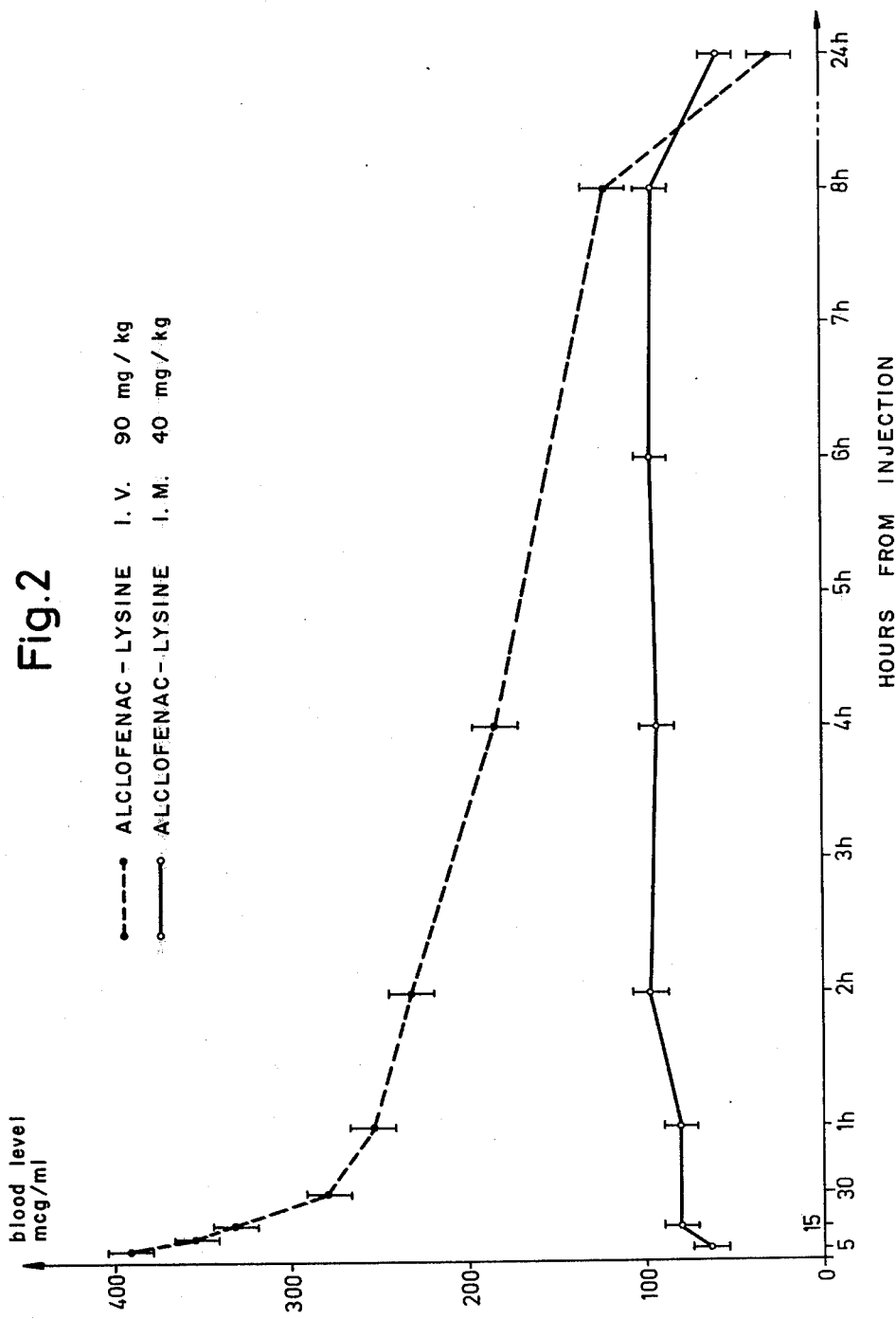

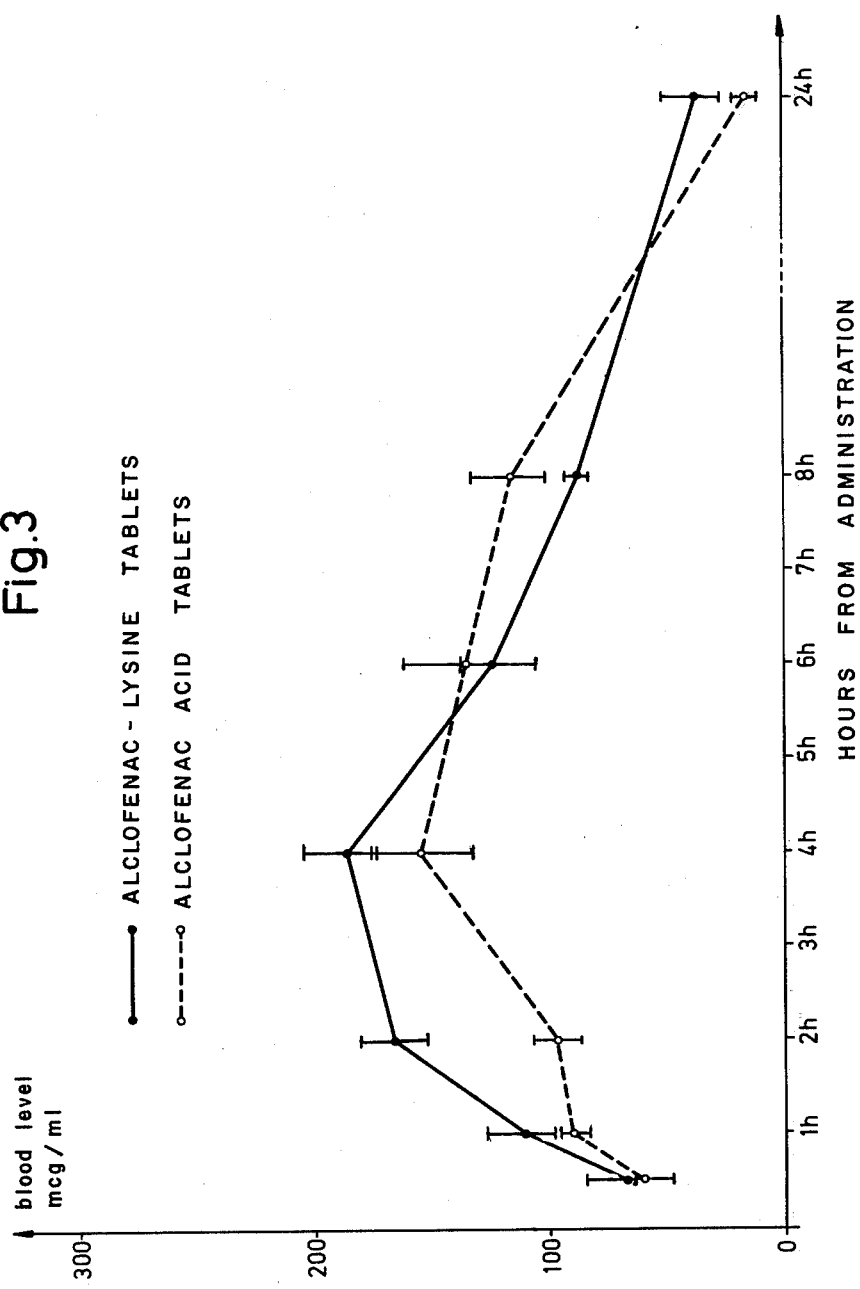

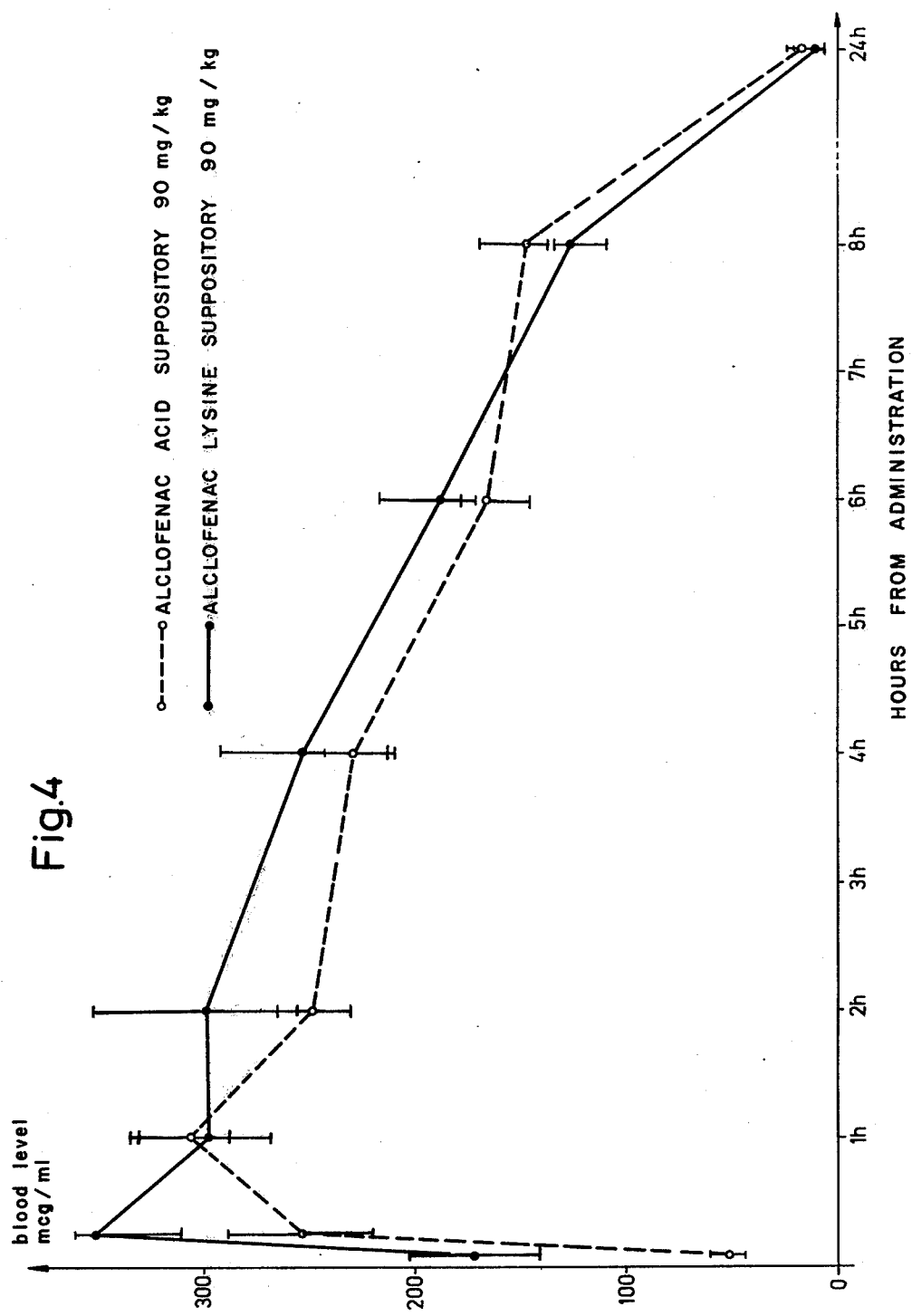

LYSINE 4-ALLYLOXY-3-CHLOROPHENYLACETATE AND METHOD OF ITS PREPARATION

This is a continuation of application Ser. No. 777,896, filed Mar. 16, 1977, now abandoned.

BACKGROUND OF THE INVENTION

The antiinflammatory properties of 4-allyloxy-3-chlorophenylacetic acid (briefly referred to as Alclofenac) are known, and its administration through the oral route has been used for some time, especially for therapy of arthrosis forms.

This drug has also a marked analgesic activity, higher than acetylsalicylic acid. Its administration through the intravenous route however is hindered by insolubility of the compound and by the fact that the sodic salt of the acid is scarcely tolerated.

To this purpose the following other solubilizations and esterifications were carried out in order to try to overcome this disadvantage.

(1)—Methylglucamine salt 16 g of N-methylglucamine are dissolved in 100 ml of water; 15 g of Alclofenac are added while stirring. When solution is complete, 600 mg of lidocaine are dissolved in the solution and volume is brought to 180 ml. A solution is obtained, which when properly filtered is injectable. As the salt in solution thus obtained is not very stable, an attempt to obtain the solid form was made. By lyophilization however a very hygroscopic salt is obtained, which may be hardly isolated.

(2)—Mono-ethanolamine solution

One mole of monoethanolamine is placed in water and while stirring one mole of Alclofenac is added. A stable, limpid, yellowish solution with pH 7.5 is obtained. The solid product is isolable only with difficulty. This solution however was discarded for its poor tolerability.

(3)—Arginine salt 15.4 g of base arginine are dissolved in 100 ml of water; 20 g of Alclofenac are added to the solution and stirring is carried on up to complete solution with pH 7.7. The filtered solution is frozen 6 hours at $-40°$ C. Then lyophilization is carried out at a temperature of $+40°$ C. A white-crystalline non-hygroscopic product is obtained, with melting point $192°-194°$ C., characteristic IR, titer 100%. However, this salt was discarded because of its intrinsic drawback of being scarcely water soluble.

On the contrary, the salt obtained from 4-allyloxy-3-chlorophenylacetic acid with lysine is a salt which is soluble in biological fluids and is well tolerated after either intravenous or intramuscular administration.

Its analgesic, antipyretic and antiinflammatory properties are equal or even superior to those of the starting acid. This happens because to the specific activity of the acid, after salification with lysine, a higher absorption velocity even through the oral and rectal route is added. It is clear that this means higher blood levels and therefore a higher therapeutic efficiency.

The lysine salt of 4-allyloxy-3-clorophenylacetic acid is also better tolerated per os, just because of its higher absorption velocity.

SUMMARY OF THE INVENTION

The present invention therefore is directed to lysine 4-allyloxy-3-chlorophenylacetate, whose structural formula is the following:

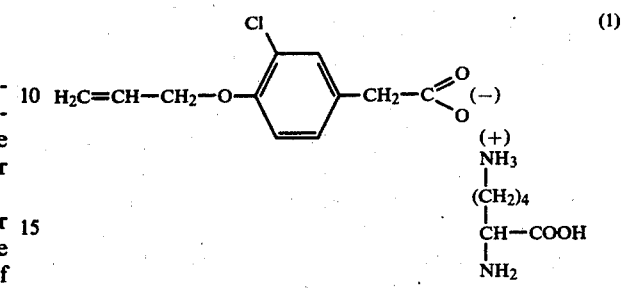

corresponding to the empirical formula $C_{17}H_{25}O_5ClN_2$ with molecular weight 372.79.

The present invention relates also to the method of preparation of the compound (1) and pharmaceutical compositions containing said compound as an active substance.

According to the present invention the compound (1) is obtained by reacting 4-allyloxy-3-chlorophenylacetic acid with lysine carbonate in hydroalcoholic solution and separating the corresponding salt by addition of precipitants or in a simpler way by concentration of the hydroalcoholic solution.

The two reagents are used in a stoichiometric quantity. The salt has the appearance of a white crystalline solid with tone on the yellowish side and characteristic odor, perfectly characterizable and it is very soluble in water and alcohols while it is insoluble in acetone. The solutions of compound (1) are perfectly stable; for the purpose of the administration through injection it is also useful to employ single dose ampuls containing the salt (1) in the lyophilized form, for instance in doses of 822.57 mg, corresponding to 500 mg of 4-allyloxy-3-chlorophenylacetic acid.

DETAILED DESCRIPTION OF THE PREFERRED EMBODIMENTS

The following examples illustrate the method of preparation according to the present invention. These examples are to be intended as merely illustrative and not limiting the scope of the invention.

EXAMPLE 1

226.6 g of 4-allyloxy-3-chlorophenylacetic acid are dissolved in 1200 ml of 25% ethyl alcohol. Separately 146 g of lysine are dissolved in water which is then, saturated with $CO_2$, so as to obtain a 30% solution of lysine carbonate.

The solutions are joined with care in order to avoid an excessive foaming due to $CO_2$ development. The mixture is then left standing 24 hours at $4°$ C. to complete the reaction.

Evaporation under vacuum to a small volume is effected. Then crystallization is effected in an ice bath while standing 72 hours. The precipitate is then recovered with some acetone and is filtered with pump. The residue is washed on the filter with ethyl ether and dried under vacuum. 205 g of lysine 4-allyloxy-3-chlorophenylacetate with 99% purity is obtained.

The compound obtained in this way is a non-hygroscopic white crystalline solid with a color tone on the yellowish side, with melting point 158°–162° C. It has a titer of 99%, determined in a volumetric way. pH value of the 10% aqueous solution is 7.7.

The data of the standard analysis correspond to the calculated ones. The UV absorption on an aqueous solution of the product with a concentration of 50 mcg/ml has a characteristic development with a maximum at 279 mµ and a minimum at 250 mµ.

EXAMPLE 2

146 g of lysine are dissolved in water and the solution is saturated with $CO_2$ so as to obtain a 30% solution of lysine carbonate. Separately 226.6 g of 4-allyloxy-3-chlorophenylacetic acid are dissolved in 800 ml of isopropyl alcohol. The two solutions are joined by pouring the alcoholic solution into the aqueous solution with light stirring. Stirring is continued 5 hours at room temperature.

This solution is then introduced into a vacuum thickener, where working at a temperature of 35° C. and a vacuum of 20 mm Hg the solution volume is concentrated up to one fourth of the original value. Vacuum is removed, solution is cooled and 1800 ml of acetone are added.

Stirring is maintained while holding temperature of the solution at +2° C., and stirring is continued 24 hours. Solution is left standing 12 hours. The obtained residue is filtered under vacuum, and washed with little acetone. 185 g (yield 49%) of the product $C_{17}H_{25}O_5ClN_2$ are obtained with the following characteristics: m.p. 158°–162° C.; K F 0.8%; Titer 99.8%.

EXAMPLE 3

120 g of lysine chlorohydrate are dissolved in 1000 ml of distilled water. The solution is passed through a column charged with Amberlite IRA 120, subsequently washing the same column with distilled water. The lysine solution, including washes, is then saturated with $CO_2$ by controlling carefully the pH value. Saturation is stopped when pH reaches about 10.7.

To this new solution 148.8 g of 4-allyloxy-3-chlorophenylacetic acid are added little by little and while stirring at room temperature, and stirring is maintained until all the acid is dissolved in the solution. At this point pH is again controlled, because pH must be maintained between 7 and 7.5.

The solution is filtered and lyophilization is effected. The lyophilized product is screened and collected is suitable containers. These last stages of preparation are effected under nitrogen atmosphere.

From the foregoing examples, the general characteristic of the product of the present invention, Alclofenac-lysine of the formula (1), may be summarized as follows:
Molecular weight: 372.79
Powder appearance: crystalline, white with yellowish tone and characteristic odor.
Melting point: 158°–162° C.
Solubility: extremely soluble in water and alcohols; insoluble in acetone.
Water content: below 1%
Purity: Product must contain not less than 25% of $C_{17}H_{25}O_5 ClN_2$
pH: Aqueous solution 25% parts/volume must have a pH of 7.4–7.8.
Identification: IR identification with Perkin Elmer apparatus shows a characteristic pattern
UV-Absorption: in aqueous solution, with concentration of 50 mcg/ml it has a characteristic development with a maximum at 279 nmµ and a minimum at 250 nmµ

The present invention succeeds in use of the mentioned specific characteristics of Alclofenac in the preparation of injectable pharmaceutical preparations.

As the Alclofenac molecule is insoluble in the physiological fluids, it is necessary to effect a transformation thereof which allows the dissolution in them. The tested solutions are the sodium salt of the acid, and its salts with methylglucamine, arginine, lysine and ethanolamine.

Apart the considerations of a chemical-physical nature, salt formation with lysine was the form chosen for the pharmacological tests because of its better tolerability at local levels.

Such a tolerability was estimated after injection of equivalent solutions of the various preparations, effected in the rabbit dorsal long muscle, removing muscle 24 hours after injection and estimating the degree of induced irritation through arbitrary scores. The results obtained are summarized in Table 1.

The results clearly indicate that the best Alclofenac soluble pharmaceutical preparation is that obtained with the lysine salt.

This type of preparation was estimated also in comparison with commercially available injectable preparations according to the method of volume increase of rat leg and results are shown in FIG. 1 of the drawings.

Alclofenac-lysine proved to be better more tolerated than a commercially available preparation obtained by solubilization with methylglucamine (Mervan).

The following pharmacological experimentation was carried out in order to estimate the comparative absorption and bioavailability through various administration routes in rabbits of Alclofenac acid and its lysine salt. These data are shown in Tables 2,3,4 and 5.

Alclofenac acid is well absorbed through the oral and rectal route so that its solubilization does not bring clear improvements in either its bioavailability or of blood levels (see FIGS. 3 and 4 of the drawings).

However, it is apparent that the lysine salt is absorbed faster and to a higher extent in comparison with the acidic substance. This appears clearly from data of partial bioavailability shown in Table 5.

Contrary to what was anticipated administration through the intramuscular route did not lead to expected results.

The time levels after intramuscular administration are shown in FIG. 2 of the drawings together with the data relating to an intravenous administration of Alclofenac-Lysine.

Velocity of absorption may be compared with that per os but the instantaneous and sustained blood levels are lower so that it seems this formulation acts as a sustained release form.

TABLE 1

RABBIT MUSCLE

| TREATMENT | mg/ml (as acid) | ml injected | SCORES at 24 hours | | | | | Average |
|---|---|---|---|---|---|---|---|---|
| Alclofenac-Arginine | 131 | 0.25 | 1.5 | 3.5 | 3 | 0 | 0 | 1.6 |
| " | 100 | 0.5 | 6.5 | 2.5 | 3 | 3.5 | | 3.9 |
| Alclofenac-Lysine | 131 | 0.25 | 2 | 3 | 4 | 4 | 0 | 2.6 |
| " | 100 | 0.5 | 2 | 3 | 2 | | | 2.3 |
| Alclofenac-Ethanolamine | 100 | 0.25 | 3 | 3.5 | 2.5 | | | 3 |
| Alclofenac-Methylglucose | 100 | 0.25 | 0 | 3 | 3 | | | 2 |
| " | 100 | 0.5 | 2 | 5 | 10 | 4.5 | | 5.4 |
| Brufen-Lysine | 131 | 0.25 | 2 | 5 | 4.5 | 4 | 7 | 4.5 |
| Liometacin | vial | 0.25 | 4 | 2 | 1 | 2 | 3.5 | 2.5 |
| " | " | 0.5 | 4.5 | 0 | | | | 2.2 |
| Mervan | " | 0.25 | 6 | 3.5 | 4.5 | 3 | 7 | 4.8 |
| Aspegic | " | 0.25 | 2 | 4 | 0 | 0 | 0 | 1.2 |
| Penetracin | " | 0.25 | 4.5 | 5 | 3.5 | | | 4.3 |

TABLE 2

Pharmacokinetic parameters of Alclofenac-Lysine salt after i.v. injection of 90 mg/kg (as acid) of the drug in rabbits.

| PARAMETERS[-1] | | RABBIT I | RABBIT II | RABBIT III | RABBIT IV | MEAN ± S.E.M. |
|---|---|---|---|---|---|---|
| A | mcg $\times$ ml$^{-1}$ | 170.51 | 151.04 | 209.59 | 131.86 | 165.7 ± 16.6 |
| $\alpha$ | min$^{-1}$ | 0.083 | 0.113 | 0.067 | 0.066 | 0.082 ± 0.011 |
| $t\frac{1}{2}\alpha$ | min | 8.5 | 6 | 10.5 | 10.5 | 9 ± 1 |
| B | mcg $\times$ ml$^{-1}$ | 269.19 | 324.95 | 269.89 | 310.16 | 293.5 ± 14.2 |
| $\beta$ | min$^{-1}$ | 0.0017 | 0.0023 | 0.0011 | 0.0026 | 0.0019 ± 0.0003 |
| $t\frac{1}{2}\beta$ | min | 408 | 301 | 630 | 266 | 401 ± 81 |
| $K_{21}$ | min$^{-1}$ | 0.051 | 0.078 | 0.038 | 0.047 | 0.053 ± 0.009 |
| $K_{12}$ | min$^{-1}$ | 0.030 | 0.034 | 0.028 | 0.018 | 0.027 ± 0.003 |
| Kel | min$^{-1}$ | 0.0027 | 0.0033 | 0.0019 | 0.0036 | 0.0029 ± 0.0004 |
| $\sqrt{1}$ | l $\times$ Kg$^{-1}$ | 0.205 | 0.189 | 0.188 | 0.204 | 0.196 ± 0.005 |
| $\sqrt{2}$ | l $\times$ Kg$^{-1}$ | 0.345 | 0.432 | 0.256 | 0.537 | 0.392 ± 0.060 |
| Vd$\beta$ | l $\times$ Kg$^{-1}$ | 0.330 | 0.274 | 0.329 | 0.285 | 0.304 ± 0.015 |
| CL | ml $\times$ Kg$^{-1}$ $\times$ min$^{-1}$ | 0.56 | 0.63 | 0.36 | 0.74 | 0.57 ± 0.08 |
| AUC Total | mcg $\times$ min $\times$ l$^{-1}$ | 160.4 | 142.6 | 248.5 | 121.3 | 168.2 ± 28 |

TABLE 3

Pharmacokinetic costants obtained from plasma levels of Alclofenac following the administration of the acid or lysine salt by different routes.

| Kinetic parameter | | ROUTES OF ADMINISTRATION | | | | |
|---|---|---|---|---|---|---|
| | | P.OS | | RECTAL | | INTRAMUSCOLAR |
| | UNITS ± E.S.M. | Acid 90 mg/kg | Lysine Salt 90 mg/kg | Acid 100 mg/kg | Lysine salt 100 mg/kg | Lysine salt 80 mg/kg |
| Ka | min$^{-1}$ | 0.0146 ± 0.0018 | 0.0174 ± 0.0047 | 0.053 ± 0.10 | 0.132 ± 0.032 | 0.0131 ± 0.0031 |
| $t\frac{1}{2}\alpha$ | min | 51.0000 ± 5.0000 | 37.0000 ± 8.0000 | 14 ± 3 | 8 ± 3 | 60 ± 11 |
| tmax | min | 173 ± 14 | 131 ± 28 | 66 ± 9 | 39 ± 11 | 277 ± 53 |
| Cmax | mcg · ml$^{-1}$ | 358.5 ± 47.8 | 454.5 ± 152.2 | 424.7 ± 11.9 | 473.7 ± 24.1 | 144.2 ± 30 |
| Kel | min$^{-1}$ | 0.0018 ± 0.0005 | 0.0023 ± 0.0005 | 0.0023 ± 0.0003 | 0.0026 ± 0.0004 | 0.0007 ± 0.0003 |
| $t\frac{1}{2}\beta$ | min | 414 ± 40 | 377 ± 92 | 307 ± 35 | 268 ± 71 | 1407 ± 378 |
| Vd$\beta$ | l · kg$^{-1}$ | 0.326 ± 0.045 | 0.301 ± 0.050 | 0.274 ± 0.060 | 0.248 ± 0.072 | 0.607 ± 0.090 |
| CL | ml · kg$^{-1}$ · min$^{-1}$ | 0.64 ± 0.06 | 0.67 ± 0.06 | 0.54 ± 0.04 | 0.55 ± 0.03 | 0.67 ± 0.06 |

TABLE 4

Extent of Availability of Alclofenac after different routes of administration using intravenous administration as reference.

| | I.V. | P.O. (acid) | P.O. (lysine salt) | Rectal (acid) | Rectal (lysine salt) | I.M. (lysine salt) |
|---|---|---|---|---|---|---|
| Practical AUC[a] | | | | | | |
| mcg · min · l$^{-1}$ ± S.E.M. | 155.6 ± 5 | 130.7 ± 14 | 137.8 ± 11 | 182.8 ± 14 | 173.3 ± 14 | 131.9 ± 26 |
| Dose (mg · kg$^{-1}$) | 90 | 90 | 90 | 100 | 100 | 80 |
| (% Availability) | 100 | 84.0 | 88.5 | 105.7 | 100.2 | 95.4 |
| Theoretical AUC[b] | | | | | | |
| mcg · min · l$^{-1}$ ± S.E.M. | 168.2 ± 28 | 150.0 ± 19 | 139.1 ± 14 | 162.9 ± 13 | 166.7 ± 12 | 231.5 ± 57 |
| Dose (mg · kg$^{-1}$) | 90 | 90 | 90 | 100 | 100 | 80 |
| (% Availability) | 100 | 89.2 | 82.7 | 87.2 | 89.2 | 154.8 |

[a]Practical AUC was calculated using the trapezoidal method. The remaining area after the last observation was calculated according to Wagner using: Ctn.Kel$^{-1}$ = Area 24h
[b]Theoretical AUC was evaluated on the fitted curve by the equations:
AUC = A/$\alpha$ + B/$\beta$ for the intravenous administration
AUC = Co/Ke for the extravascular administration

TABLE 5

Extent of Availability of Alclofenac after different routes of administration using intravenous administration as reference.

|  | AUC o → 4h | | | |
|---|---|---|---|---|
|  | I.V. | P.O. Acid | P.O. Lysine | F Lys. vs acid |
| Practical AUC mcg · min · $l^{-1}$ ± S.E.M. | 55.85 ± 2.3 | 23.69 ± 1.5 | 32.45 ± 2 | — |
| Dose (mg · $kg^{-1}$) | 90 | 90 | 90 | — |
| (% Availability) | 100 | 42.4 | 58.12 | <0.01 |

|  | AUC o → 2h | | | |
|---|---|---|---|---|
|  | I.V. | Rectal acid | Rectal Lys. | F Lys. vs acid |
| Practical AUC mcg · min · $l^{-1}$ ± S.E.M. | 33.15 ± 1 | 30.6 ± 1.7 | 35.23 ± 2.6 | — |
| Dose (mg · $kg^{-1}$) | 90 | 100 | 100 | — |
| (% Availability) | 100 | 83.24 | 95.65 | ns |

Taking into account also the chemical-physical characteristics of Alclofenac lysine salt, it is be considered to be appropriate for preparations intended for intravenous use. Its appropriateness for forms to be administered per os is retained when these forms require the presence of the drug in a solution.

Furthermore, the shorter residence time at the gastric level enables a better tolerance of the preparation.

The intramuscular form may be considered appropriate when it should be used just as a sustained release preparation for particular therapeutic uses.

Typical examples of formulas for compositions containing Alclofenac-lysine salt as the active ingredient are as follows:

(1) Injectable product

Each vial contains:
Alclofenac lysine—824 mg
Lidocaine—10 mg
Septocombin—5 mg
Mannitol—400 mg

(2) Products for oral use (A) Syrup containing per 100 ml:
Alclofenac lysine—5 g
Glycerine—2 g
Sodium Septocombin—0.5 g
Flavored sugar syrup q.s. ad 100 ml
(B) Single dose bag
Each bag contains:
Alclofenac lysine—900 mg
Flavored granulate q.s. ad—3 g

(3) Rectal form product

Each suppository contains:
Alclofenac lysine—900 mg
Miogliol 812—100 mg
Witeposal W31 q.s. ad—3 g

(4) Ointment form product 100 g of product contain:
Alclofenac lysine—9 g
Stearic acid—10 g
Pul. sorbitan monostearate—6 g
Sorbitan monostearate—1 g
Propyleneglycol—1 g
Preserver—0.5 g
Water q.s. ad—100 g From the foregoing it is apparent that the lysine salt of Alclofenac according to the present invention unexpectedly shows for superior properties and characteristics, rendering it a unique antiinflammatory and analgesic drug, especially adapted for intravenous administration.

We claim:

1. Lysine 4-allyloxy-3-chlorophenylacetate having the following structural formula:

$$H_2C=CH-CH_2-O-\underset{}{C_6H_3(Cl)}-CH_2-COO^{(-)}$$

$$^{(+)}NH_3-(CH_2)_4-CH(NH_2)-COOH \quad (I)$$

corresponding to the empirical formula $C_{17}H_{25}O_5ClN_2$ with molecular weight 372.79.

2. A well-tolerated pharmaceutical syrup, injectable, oral, rectal, or ointment composition suitable for use as an anti-inflammatory and analgesic, containing as active substance an effective anti-inflammatory and analgesic amount of lysine-4-allyloxy-3-chlorophenylacetate.

3. A well-tolerated injectable pharmaceutical syrup, injectable, oral, rectal, or ointment preparation suitable for use as an anti-inflammatory and analgesic, containing an active substance an effective anti-inflammatory and analgesic amount of lysine-4-allyloxy-3-chlorophenylacetate in lyophilized form.

4. A method which comprises administering to a patient an effective and relatively well-tolerated analgesic or antiinflammatory amount of a compound according to claim 1.

* * * * *

UNITED STATES PATENT AND TRADEMARK OFFICE
CERTIFICATE OF CORRECTION

PATENT NO. : 4,189,499

DATED : February 19, 1980

INVENTOR(S) : Carlo Tosi and Pierarturo Ferlenghi

It is certified that error appears in the above—identified patent and that said Letters Patent is hereby corrected as shown below:

Col. 7, line 20; "it is be considered" the -- be -- should be deleted.

Col. 8, line 54; "an" (first occurrence) should read -- as --

Signed and Sealed this

Twenty-ninth Day of July 1980

[SEAL]

Attest:

SIDNEY A. DIAMOND

Attesting Officer     Commissioner of Patents and Trademarks